(12) United States Patent
Sahin et al.

(10) Patent No.: US 9,655,990 B2
(45) Date of Patent: May 23, 2017

(54) POLYMER BASED HYDROGEL

(71) Applicant: YEDITEPE UNIVERSITESI, Istanbul (TR)

(72) Inventors: Fikrettin Sahin, Istanbul (TR); Selami Demirci, Istanbul (TR); Aysegul Dogan, Istanbul (TR)

(73) Assignee: YEDITEPE UNIVERSITESI, Istanbul (TR)

( * ) Notice: Subject to any disclaimer, the term of this patent is extended or adjusted under 35 U.S.C. 154(b) by 0 days.

(21) Appl. No.: 14/783,081

(22) PCT Filed: Apr. 8, 2014

(86) PCT No.: PCT/TR2014/000136
§ 371 (c)(1),
(2) Date: Oct. 7, 2015

(87) PCT Pub. No.: WO2014/168595
PCT Pub. Date: Oct. 16, 2014

(65) Prior Publication Data
US 2016/0051724 A1   Feb. 25, 2016

(30) Foreign Application Priority Data

Apr. 8, 2013   (TR) .............................. a 2013 04209

(51) Int. Cl.
| | | |
|---|---|---|
| *A61L 26/00* | (2006.01) | |
| *A61K 9/00* | (2006.01) | |
| *A61K 47/32* | (2006.01) | |
| *A61L 15/26* | (2006.01) | |
| *A61L 15/44* | (2006.01) | |
| *A61L 15/46* | (2006.01) | |
| *A61K 47/34* | (2017.01) | |
| *A61K 8/04* | (2006.01) | |
| *A61K 8/19* | (2006.01) | |
| *A61K 8/84* | (2006.01) | |
| *A61Q 17/00* | (2006.01) | |
| *A61Q 19/08* | (2006.01) | |
| *C08K 3/38* | (2006.01) | |

(52) U.S. Cl.
CPC .......... *A61L 26/0019* (2013.01); *A61K 8/042* (2013.01); *A61K 8/19* (2013.01); *A61K 8/84* (2013.01); *A61K 9/0014* (2013.01); *A61K 47/32* (2013.01); *A61K 47/34* (2013.01); *A61L 15/26* (2013.01); *A61L 15/44* (2013.01); *A61L 15/46* (2013.01); *A61L 26/0004* (2013.01); *A61L 26/008* (2013.01); *A61L 26/0066* (2013.01); *A61Q 17/005* (2013.01); *A61Q 19/08* (2013.01); *C08K 3/38* (2013.01); *A61L 2300/10* (2013.01); *A61L 2300/404* (2013.01); *A61L 2300/412* (2013.01); *C08K 2003/387* (2013.01)

(58) Field of Classification Search
CPC .................................................. A61L 26/0019
USPC ......................................................... 514/784
See application file for complete search history.

(56) References Cited

U.S. PATENT DOCUMENTS

2010/0286010 A1   11/2010   Xia et al.

FOREIGN PATENT DOCUMENTS

| CN | 102885768 A | 1/2013 |
|---|---|---|
| GB | 2362100 A | 11/2001 |

OTHER PUBLICATIONS

Kim et al., Arch. Pharm. Res. (2007), vol. 30(3), pp. 381-386.*
Ai-Bayaty, Fouad, and Mahmood Ameen Abdulla. "A Comprarison of Wound Healing Rate Following Treatment with Aftamed and Chlorine Dioxide Gels in Streptozotocin-Induced Diabetic Rats." Evidence-Based Complementary and Alternative Medicince 2012(2012).
Auf Dem Keller, Ulrich, et al. "Reactive Oxygen species and their detoxification in healing skin wounds." Journal of Investigative Dermatology Symposium Proceedings. vol. 11.No.1. Nature Publishing Group,2006.
Bartosz, Grzegorz. "Reactive Oxygen species: destroyers or massengers?, " Biochemical Pharmacology 77.8(2009): 1303-1315.
Batrakova, Elena V., and Alexander V. Kabanov. "Pluronic block copolymers: evolution of drug delivery concept from inert nanocarriers to biological response modifiers." Joural of Controlled Release 130.2(2008):98-106.
Baum, Christian L., and Christopher J. Arpey "Normal cutaneous wound healing:clinical correlation with cellular and molecular events." Dermatologic Surgery 31.6(2006):674-686.
Benderdour, M., et al. "Effects of boron derivatives on extracellular matrix formation." Journal of trace elements in medicine and biology 14.3(2000):168-173.
Benderdour, M., et al. "Boron modulates extracellular matrix and TNFα synthesis in human fibroblasts." Biochemical and biophysical research communications 246.3(1998)746-751.
Benderdour, Mohamed., et al. "Effect of boric acid solution on cartilage metabolism". Biochemical and biophysical research communications234.1(1997): 263-268.
Bowler, P.G., B.I. Duerden,and D.G. Armstrong. "Wound microbiology and associated approaches to wound management." Clinical microbiology reviews 14.2(2001):244-269.

(Continued)

*Primary Examiner* — Taofiq A Solola
(74) *Attorney, Agent, or Firm* — Gokalp Bayramoglu (57) ABSTRACT

The present invention relates to an anti-aging antimicrobial wound healing polymer based hydrogel. In the study of the present invention, a wound healing gel formulation is developed by combining poloxamer polymers and boron component at adequate concentrations in a carbopol based gel. The said gel exhibits fast action on the damaged area and prevents scar formation.

8 Claims, 8 Drawing Sheets

(56) References Cited

OTHER PUBLICATIONS

Brett, David. "A review of collagen and collagen-based wound dressings." Wounds 20.12(2008):347-353.

Chebassier,Nathalie,et al."In vitro induction of matrix metalloproteinase-2 and matrix metalloproteinase-9 expression in keratinocytes by boron and manganese." Experimental dermatology 13.8(2004):484-490.

Clark, Richard AF."Fibronectin matrix deposition and fibronectin receptor expression in healing and normal skin." Journal of Investigative Dermatology 94(1990):128s-134s.

Diegelmann, Robert F.,and Melissa C. Evans. "Wounding healing: an overviw of acute, fibrotic and delayed healing." Front Biosci9. 1(2004):283-289.

Ellis, Ian R.,et al. "Migration Stimulating Factor(MSF) promotes fibroblast migration by inhibiting AKT." Cellular signalling22. 11(2010):1655-1659.

Fernandes, Desmond,and Massimo Signorini,"Combating photoaging with percutaneous collagen induction." Clinics in dermatology 26.2(2008):192-199.

Gordillo, Gayle M.,and Chandan K. Sen. "Revisiting the essential role of oxygen in wound healing." The American journal of surgery 186.3(2003):259-263.

Hotel-Dieu, Place A. Ricordeau, and FR44035 Nantes. "Stimulatory effect of boron and manganese salts on keratinocyte migration." Acta Derm Venereol 84 (2004): 191-194.

Kabanov, Alexander V., et al. "Micelle formation and solubilization of fluorescent probes in poly (oxyethylene-b-oxypropylene-b-oxyethylene) solutions," Macromolecules 28.7 (1995): 2303-2314.

Lalitha, M. K. "Manual on antimicrobial susceptibility testing;" URL: http ://www.ijmm. org/documents/Antimicrobial. doc (2005).

Masaki, Hitoshi. "Role of antioxidants in the skin: anti-aging effects." Journal of dermatological science 58.2 (2010): 85-90.

McPherson JM, Piez KA. Collagen in dermal wound repair.In: Clark RAF Henson PM editors. The molecular and cellular biology of wound repair. New York: Plenum Press1988: 471-91.

Munz, B. et al. "A novel type of glutathione peroxidase: expression a regulation during wound repair." Biochemical Journal 326.Pt 2 (1997): 579.

Nzietchueng, Rosine Mayap, et al."Mechanisms implicated in the effects of boron on wound healing." Journal of trace elements in medicine and biology 16 .4(2002):239-244.

O'Toole Edel A., Mimi Goel and David T. Woodley. "Hydrogen peroxide inhibits human keratinocyte migration," Dermotologic surgery:official publication for American Societyfor Dermatologic Surgery [et al.] 22.6 (1996): 525.

Panchatcharam,Manikandan,et al."Curcumin improves wound healing by modulating collagen and decreasing reactive oxygen species," Molecular and cellular biochemistry 290.1(2006):87-96.

Pillai,S.,C.Oresajo, and J. Hayward. "Ultraviolet radiation and skin aging: roles of reactive oxygen species inflammation and protease activation, and strategies for prevention of inflammation induced matrix degradation—a review," International journal of cosmetic science 27.1(2005): 17-34.

Ramirez, Octavio T., and R. Mutharasan "The role of the plasma membrane fluidity on the shear sensitivity of hybridomas grown under hydrodynamic stress." Biotechnology and bioengineering 36.9 (2004): 911-920.

Robson, Martin C. "Wound infection: a failure of wound healing caused by an imbalance of bacteria." Surgical Clinics of North America 77.3 (1997): 637-650.

Schultz, Gregory S.and Annette Wysocki. "Interactions between extracellular matrix and growth factors in wound healing" Wound Repair and Regeneration17.2 (2009): 153-162.

Singer, Adam J. and Richard AF Clark. "Cutaneous wound healing ." New England journal of medicine 341.10 (1999): 738-746,.

Steiling, Heike, et al. Different types of ROS-scavenging enzymes are expressed during cutaneous wound repair. Experimental cell research 247.2 (1999): 484-494.

Takasao, Naoko,et al. "Cinnamon extract promotes type 1 collagen biosynthesis via activation of IGF-I signaling in human dermal fibroblasts," Journal of agricultural and food chemistry 60.5 (2012): 1193-1200.

Walter, M. N. M.,et al."Mesenchymal stern cell-conditioned medium accelerates skin wound healing: An in vitro study of fibroblast and keratinocyte scratch assays." Experimental cell research 316.7 (2010): 1271-1281.

Yalvac, Mehmet E. , et al. "Comparison and optimisation of transfection of human dental follicle cells, a novel source of stem cells, with different chemical methods and electro-poration." Neurochemical research 34.7 (2009): 1272-1277.

Yalvac, Mehmet E., et al. "Human tooth germ stem cells preserve neuro-protective effects after long-term cryo-preservation." Curr Neurovasc Res 7 (2010): 49-58.

Yalvac Mehmet E. et al. "Differentiation and Neuro-Protective Properties of Immortalized Human Tooth Germ Stem Cells." Neurochemical research 36.12 (2011): 2227-2235.

Zoutman Dick Shirley McDonald and Dilini Vethanayagan. "Total and attributable costs of surgical-wound infections at a Canadian tertiary-care center." Infection control and hosplital epidemiology (1998): 254-259.

\* cited by examiner

POLYMER BASED HYDROGEL

FIELD OF THE INVENTION

The present invention relates to an anti-aging antimicrobial wound healing polymer based hydrogel

BACKGROUND OF THE INVENTION

The basic function of the skin is to create a barrier which can protect the body against environmental damages and effects, and to ensure homeostasis. Thus, any deformation that may occur in the skin integrity may leave the human body vulnerable against many pathological situations such as infection, extreme dehydration, electrolyte imbalance, etc. (Baum and Arpey, 2005). For this reason, large damages that may occur on the skin due to diseases or injuries cause serious dysfunctions and even deaths (Singer and Clark, 1999). Immediately after impairment of skin integrity, wound healing starts in the body. This is a complex event where a series of biological events regularly follow each other, and it mostly ends up with partial or complete regeneration of the tissue. Generally, wound healing is comprised of four interconnected phases which are homeostasis, inflammation, proliferation and remodeling (Diegelmann and Evans, 2004). Even though the organism is organized to close and remodel the wound, many factors independent of the organism may delay the process by affecting wound healing and cause formation of chronic wounds. For example, microbial, contamination that may occur at the wound area and the products (endotoxin, metalloproteinase, etc.) formed by these microorganisms may impede restoring skin integrity by affecting the healing process negatively (Robson, 1997). As the microbial colonization forming on the wound surface is a poly-microbial environment accommodating many pathogens, the risk of infection of the wound is high (Bowler et al., 2001). Infection of the wound delays wound healing and cause the trauma to increase, and the treatment processes to be more complex and costly.

Zoutman et al. have shown with the study they have conducted that wound infection increases length of hospitalization of the patient averagely by 10.2 days and that this brings an additional cost of $3,937 per patient (1998).

In order to prevent contamination of the wound area by any microorganism, the immune system cells stimulated by growth factor and cytokines migrate to the wound area. In the inflammation step which takes place right after the wound occurs, neutrophils and macrophages arrive at the wound area. In addition to these, lymphocytes and monocytes also go to the wound area, transform into macrophages and help the defense system. The neutrophils and macrophages that have reached the wound area inhibit the microorganisms at the wound area by producing a high amount of reactive oxygen species (ROS) (Gordillo and Sen, 2003). If there is extreme microbial contamination in the wound area, neutrophil and macrophage densities increase and these cells, which produce excessive amounts of ROS, cause tissue and cell destruction. This destruction delays wound healing. The reactive oxygen species interact with DNA, protein and lipids and cause degradation of them. The ROS species bind to DNA and cause double or single strand breakdowns and mutations (Bartosz, 2008). In addition to that, they cause lysis of the cells by causing ROS lipid peroxidation (Panchatcharam et al., 2006). Another example of negative impacts of ROS species on wound healing is the fact that ROS species such as hydrogen peroxide reduce proliferation and migration of many cells such as keratinocytes (O'Toole et al. 1996). However certain adaptations have developed against ROS species in order to maintain skin integrity. ROS detoxification is provided by two different strategies in the cell. ROS is eliminated by small antioxidant molecules such as Poly-unsaturated fatty acid, ascorbate or sugars (mostly mannitol) or with superoxide dismutase (SOD), catalase and various peroxidases (e.g. glutathione peroxidase) (Steiling et ah, 1999). Among these enzymes, superoxide dismutase (SOD) enables transformation of superoxide radical anion, which is mostly formed in the wound healing process, to hydrogen peroxide (Ulrich et al., 2006). Even though hydrogen peroxide is not radical, it should be immediately decomposed because of its capacity of transforming to hydroxyl radical. Reaction of reducing hydrogen peroxide to water is generally performed with the help of catalase and glutathione enzymes. During wound healing, if the amount of these enzymes is less than that of ROS species, they cause DNA damage, protein and lipid peroxidation at the wound area and thus delay wound healing.

Cellular communication, extracellular matrix (ECM) formation, growth factors and cytokine release should be complete for a complete healing in the process of wound healing. ECM formation is included almost in the entire wound healing process and has an important place. Generally, the components forming ECM are synthesized and combined outside of the cell surface and thus provide structural and functional integrity to connective tissues and organs. ECM synthesis and storing out of the cell are enabled by the signal, transmission means, growth factors and cytokine release provided by means of cell surface receptors (Schultz and Wysocki, 2009). Fibroblast cells synthesize various collagen types right after wound formation in order to recover the damage that has occurred in the tissue and to maintain integrity (McPherson and Piez, 1988). Collagen type 1 and 3 provide tensile strength of the skin and thereby enable the skin to be strong and resistant against mechanical stress.

At first, collagen was thought to be necessary only for maintaining skin integrity, however new studies have shown that collagen is also important for synthesis of many proteins required for the cell form and differentiation, migration and wound healing (Brett, 2008). In order to ensure an effective migration of keratinocytes, there must be sufficient amount of collagen type 1 at the wound area.

Another important extracellular matrix protein is fibronectin. Fibronectin, which is an adhesive glycoprotein synthesized by the cells at the wound area, serves for cell adhesion, growth, cell migration and differentiation. Fibronectin acts as a biological adhesive due to its molecular structure and functions as an important bridge for the cell to communicate with the other extracellular matrix proteins (Clark, 1990). Fibronectin and fibrin enable cell adhesion and migration by producing a temporary matrix at the wound area. However when dermalepidermal regeneration is completed, fibronectin mostly remains limited with the basal membrane region of the dermal-epidermal connection region (Schultz and Wysocki, 2009). Thus, fibronectin has effects that vary according to certain steps of wound healing.

Increase of remodeling and synthesis of ECM also delays aging on the skin. As the ECM layer on the aging skin becomes more fragile, wrinkles occur. The skin composition which has aged due to internal or external factors may have been caused by a reduction of the amount or a deformation of ECM in the dermis layer (Takasao et al., 2012). Thus, induction of collagen type 1, which constitutes 90% of ECM composition in the dermis layer, and elastic fiber synthesis enables the skin to stay young by slowing down aging (Fernandes and Signorini, 2012).

Not only ECM deficiency but also ROS redundancy plays a large role in aging. ROS, occurring due to environmental conditions, causes increase (up-regulation) of the matrix metalloproteinases that particularly serve for ECM destruction by increasing inflammation on the skin (Pillai et al., 2005). In addition to causing inflammation, ROS derivatives result, in damages on the skin surface by causing protein carbonylation and lipid peroxidation (Masaki, 2010). For these reasons, since increasing the activities of the enzymes (e.g. SOD, glutathione peroxidase and catalase) serving for ROS elimination will reduce the breakdowns that might occur in the skin, it will slow down aging.

Although boron is an important trace element for plants, its activity and mechanism on mammalian system has not been completely understood. In several studies conducted up to date, it is claimed that several compounds containing boron can be effective in the process of wound healing It was observed that topical administration of 3% boric acid on wounds reduced length of stay in intensive care units by three times (Nzietchueng et al., 2002). Additionally, it has been, shown in in vitro studies that boric acid increases extracellular matrix proteins (Benderdour et al., 1998). It was claimed that boric acid reduces synthesis of intracellular molecules (proteoglycan, collagen and proteins) and increases release of these molecules to culture medium (Benderdour et al., 1997). Apart from this, although it was found that four different compounds (triethanolamine borate; N-diethyl-phosphoramidate-propylboronique acid; 2,2 dimethylhexyl-1,3-propanediol-aminopropylboronate and 1,2 propanediolaminopropyl-boronate) which are boron derivatives provide more extracellular matrix protein than boric acid, it was also stated that these compounds are more toxic than boric acid (Benderdour et al., 2000).

It was shown in the in vitro studies that were conducted that sodium borate compound, which is another boron compound, increases cell migration although it does not have proliferative effect on human keratinocytes (Chebassier et al., 2004a) and increases the levels of metalloproteinase-2 (MMP-2) and matrix metalloproteinase-9 (MMP-9) enzymes which serve for dermal cell migration and granulation tissue modeling which are important steps in wound healing process (Chebassier et al., 2004b).

Poloxamers are synthetic polymers which have a triblock structure composed of hydrophobic polypropylene oxide and hydrophilic polyethylene oxide units. Poloxamer can be used for carrying therapeutic agents, drugs and genes (Batrokova and Kabanov, 2008). Due to their amphophilic structures, they serve as surfactants and can interact with membranes. In solutions, they can absorb drags and can be used for carrying thereof by forming micelle at concentrations above critical micelle concentration (Kabanov et al., 1995). They can be used in bioreactors for enhancing cell viability and decreasing agitation stress (Ramirez and Mutharasan, 1990).

The United States patent document numbered US2010286010, one of the applications known in the art, discloses an aqueous solution for cleaning and disinfecting contact lenses.

SUMMARY OF THE INVENTION

An objective of the present invention is to provide an antimicrobial polymer based hydrogel.

Another objective of the present invention is to provide an anti-aging polymer based hydrogel.

A further objective of the present invention is to provide a wound healing polymer based hydrogel.

Another objective of the present invention is to provide a polymer based hydrogel fast acting at the injured area.

A further objective of the present invention is to provide a polymer based hydrogel which prevents scar formation and enables rapid wound closure at the area where it is applied.

Another objective of the present invention is to provide a low-cost polymer based hydrogel.

BRIEF DESCRIPTION OF THE DRAWINGS

"Polymer based hydrogel" developed to fulfill the objectives of the present invention is illustrated in the accompanying figures, in which.

DETAILED DESCRIPTION OF THE INVENTION

In the study of the present invention, a wound healing gel formulation is developed by combining poloxamer polymers and boron component in a carbopol based gel.

Experimental Study

Preparation of the Gel

The gel which will be used as a carrier for the active molecules, is prepared by using 1% carbopol. In preparation of the gel, the distilled water, to which 1% carbopol is added, is left for hydration at room temperature. In the process of hydratation, carbopol is gelated by adding 1.6 grams of 18% NaOH to a completely water saturated 1 liter solution. 3% boron compound and 4% poloxamer were added to the gel mixture which was homogenized by mixing after hydratation was completed. The mixture was stored at 4° C. for 16-24 hours and made ready for use.

In the preparation of the hydrogel of the present invention, sodium pentaborate pentahydrate was specially preferred as the boron compound. Apart from this compound; boric acid, alkaline and alkaline earth metal borates and all hydrate forms of these borates, ammonium borates, boric acid esters can also be used.

Analysis Studies

Disc Diffusion Method

Antimicrobial property of the developed hydrogel composition was tested according to disc diffusion method which is described previously in the literature (Lalitha and Vellore, 2005). The 100 µl solution containing $10^8$ cfu/mil of bacteria, $10^6$ cfu/ml of yeast and $10^4$ spore/ml of fungi was prepared with new cultures and was inoculated with spreading method on Nutrient Agar (NA), Sabouraud Dextrose Agar (SDA) and Potato Dextrose Agar (PDA), respectively. 20 µl hydrogel combination was introduced on the empty discs which were then placed on the inoculated media. Hydrogel not containing the active ingredient was used as the negative control. As for positive control. Ofloxacin (10 µg/disc) and nystatin (30 µg/disc) were used for bacteria and fungi, respectively. The inoculated petri dishes were incubated for 24 hours for bacteria and 48 hours for yeasts at 36±1° C. and 72 hours for fungi at 25±1° C. Antimicrobial activity against microorganisms tested in disc diffusion method was assessed by measuring the inhibition zone.

Determining Cell Toxicity

Figure 1:
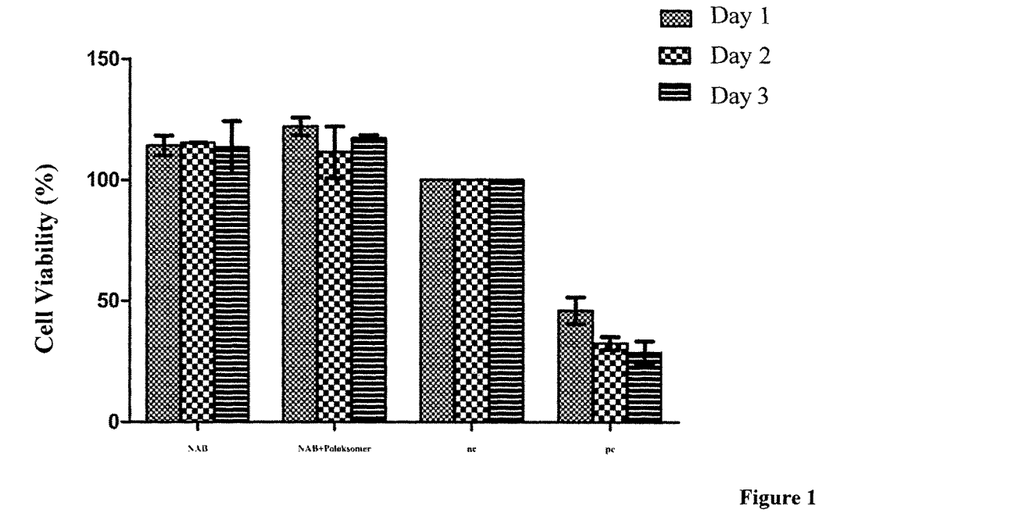
FIG. 1 shows the effect of the combination of 15 µg/ml NAB and poloxamer on L929 cell viability (NAB: Sodium pentaborate pentahydrate; NAB+Poloxamer: Gel).

Toxic effect of the prepared gel combination was determined by using the MTS (3-(4,5-dimethyl-thiazol-2-yl)-5-(3-carboxy-methoxyphenyl)-2-(4-sulfo-phenyl)-2H-tetrazolium) method given. In the literature (Yalvac et al., 2009). The molecules used in the gel were prepared alone or in combination in the medium and applied on the L929 (Mouse Fibroblast), HF (Human Fibroblast) and human keratinocyte cell lines which were seeded on 96-well culture plates (5000 cells/well) by counting. The response of the cells to toxicity of the molecules was determined by measuring cell viability for 3 days. Cell viability was determined by using a method called MTS which measures mitochondrial dehydrogenase enzyme activity of the cell. The MTS substance added onto the cells together with the medium results in colored formazan crystals formation as an indicator of cell viability. The resulting color change was evaluated based on the absorbance measurement, by using ELISA plate reader (FIG. 1, 2, 3, 4, 5). The obtained results were analyzed.

Wound Healing Scratch Model

In order to determine the effect of the gel on wound healing, its capacity for cell migration and wound closure was analyzed by using the scratch assay described in the literature (Walter et al. 2010). In in vitro wound healing model, L929 (Mouse Fibroblast), HF (Human Fibroblast) and human keratinocyte cell lines and L929-HUVEC co-culture were used. The cells were seeded onto 12 well culture plates at a concentration of 100,000 cells/well, and by storing them in a carbon dioxide incubator so that they were enabled to attach and reach the sufficient density. Scratches were formed by using 200 µl pipette tip such that they will be perpendicular to the horizontal lines drawn by an acetate pen from the center of the wells to the outside of the wells. Gel combination was applied on the cells and scratch closure was observed. Setrach closure (FIG. 6-7) was analyzed by using NIH Image program upon photographing the regions of the straches which correspond to the lines drawn by an acetate pen and which are in the field of view of the microscope at 0, 12 and 24 hours.

Real Time PCR

Real time PCR (Polymerase Chain Reaction) analyses were performed according to the literature by using SYBR Green method (Yalvac et al, 2010). The primers belonging to the collagen, fibronectin, laminin, Akt, Bax and P53 genes were designed using Primer BLAST software (The National Center for Biotechnology=NCBI). Total RNAs were isolated from the cells on which gel combination was applied and cDNA was synthesized. The synthesized cDNAs were mixed with primers in SYBR Green mix solution such that the final volume will be 20 µl and the expression levels of the genes (FIG. 8) were analyzed by using BIO-RAD device.

Examination of Oxidative Stress Parameters

Figure 9:
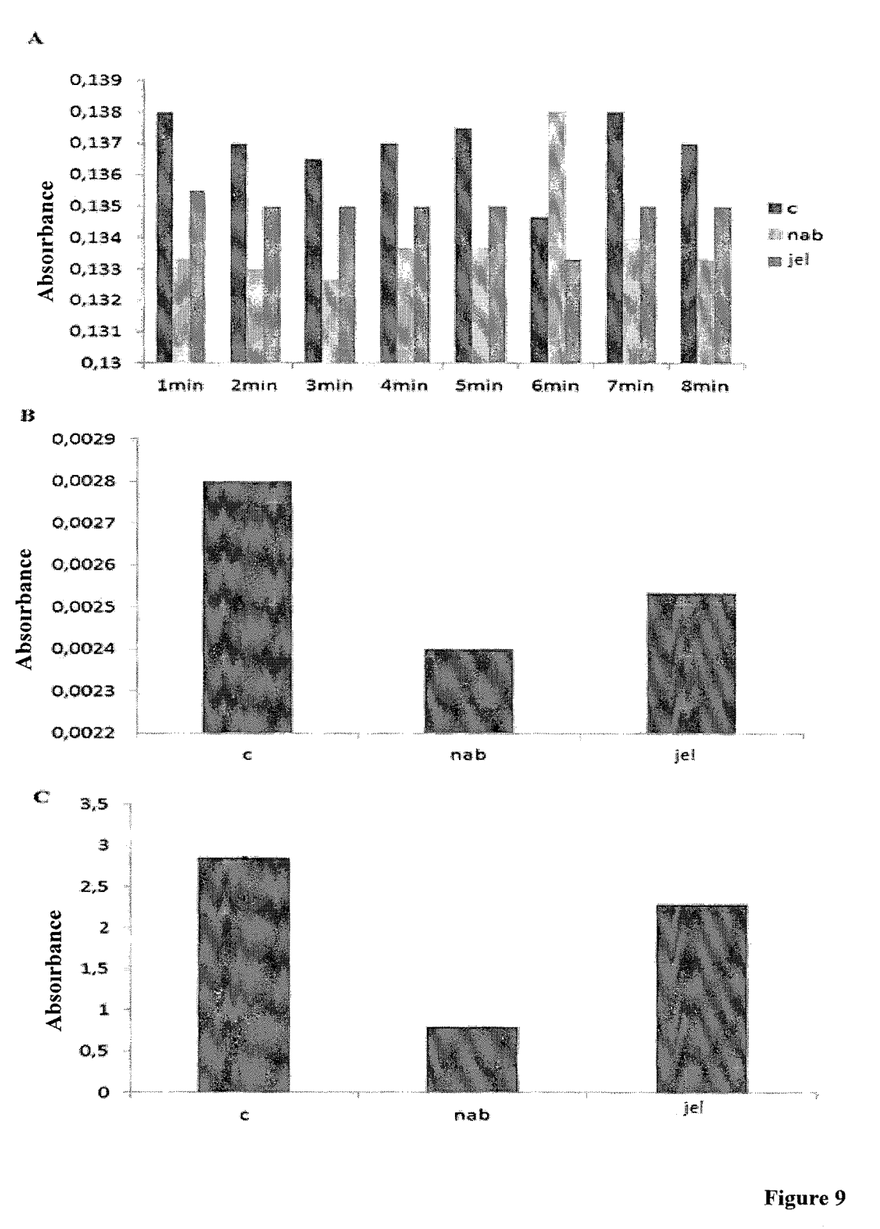
FIG. 9 is the view of the results of (a) glutathione peroxidase, (b) superoxide dismutase and (c) malondialdehyde levels.

Antioxidant parameters were determined by glutathione peroxidase and superoxide dismutase enzyme activity assay and analysis of the MDA (malondialdehyde) levels. The cells which were subjected to the gel combination, to the active agent and only to the medium for control purposes in 6-well culture plates were collected and protein isolation was performed from the cell pellet by determined by measuring absorbance and drawing a standard curve at 595 nm wavelength with Bradford solution in 96-well ELISA plates by using bovine albumin protein standards (0.125, 0.25, 0.5, 0.75, 1.0, 1.5, 2.0 mg/ml). The enzyme activity assays and MDA levels were determined such that they wilt comply with the protocols given in commercials kits (FIG. 9).

Chromosomal Analyses

Figure 10:
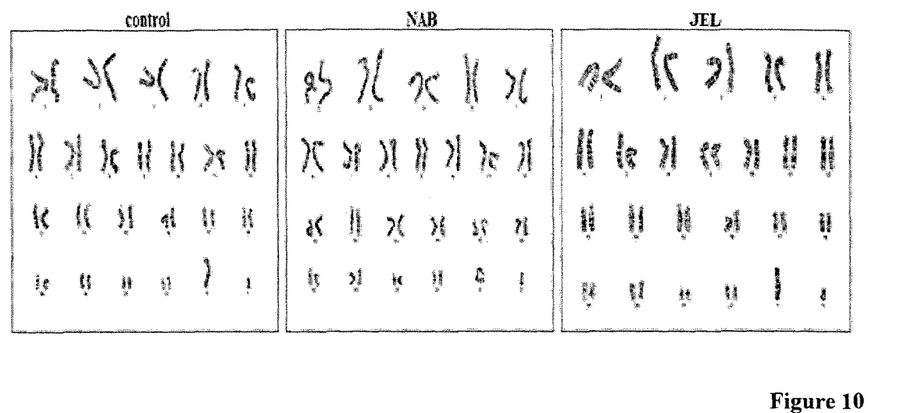
FIG. 10 is the view of karyotype analysis results of human fibroblast cells.

Whether the gel combination causes chromosomal anomaly was determined by using cyto-genetic analyses according to the literature (Yalvac et al., 2011). The cells were grown to a concentration of 50% in T-75 cell culture plates such that there is an active ingredient group and control group. The cells were primarily stored in a chromosome dissolving solution for 2.45 hours and then in a metaphase arresting solution for 75 minutes. After the cells were collected with trypsin, they were fixed with Carney fixative, spread on glass slides, incubated at 65° C. overnight, stained with Giemsa and metaphase appearances thereof were analyzed by means of a light microscope (FIG. 10).

Experimental Results

In vitro cell viability analyses were performed on L929 cells (mouse fibroblast cells) with the purpose of determining the toxic effects of the molecules, alone or in combination, in the gel mixture composed of sodium pentaborate pentahydrate and poloxamer polymer combination. It was observed that 15 µg/ml sodium pentaborate pentahydrate and poloxamer mixture, which was used in the preparation of the gel, did not have toxic effect on the mouse fibroblast cells used as model cells in wound healing experiments. After the MTS analyses that were performed for a period of three days, it was determined that the gel combination and the substances used in its composition did not have toxic effect (FIG. 1).

Figure 2:
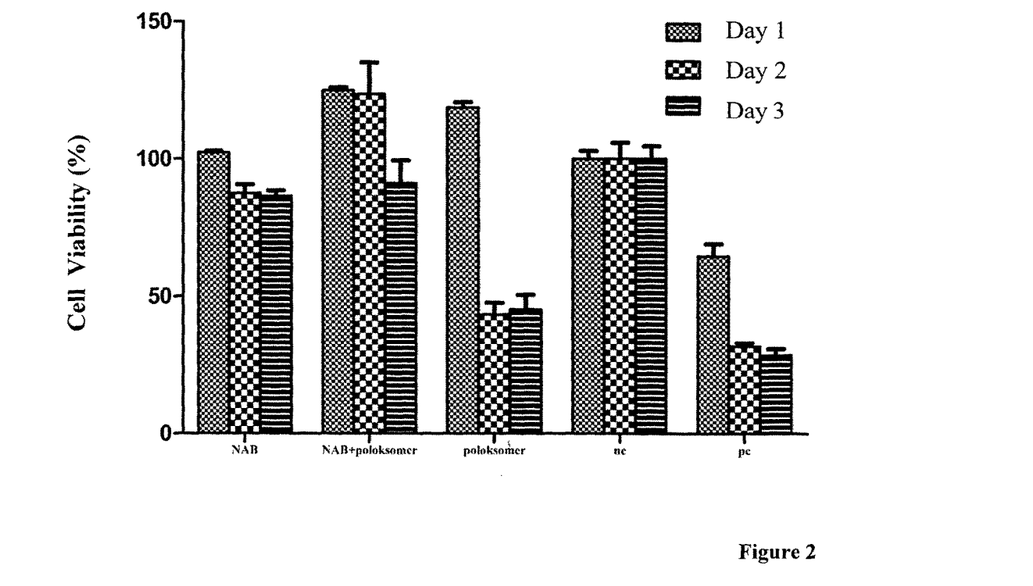
FIG. 2 shows the time dependent effect of 15 µg/ml NAB and poloxamer combinations on L929 cell viability (NAB: Sodium pentaborate pentahydrate; NAB+Poloxamer: Gel).

The toxicity analyses were repeated in order to find out the time dependent effect and the suitable metabolization period for the gel with the concentrations and combinations used in cell viability analyses. MTS experiments were made with L929 cells at 3, 6, 9 and 12 hours and optimum activity period was determined. After the analyses, it was determined that the application of 9 hours was the time period in which maximum activity was observed (FIG. 2).

Figure 3:
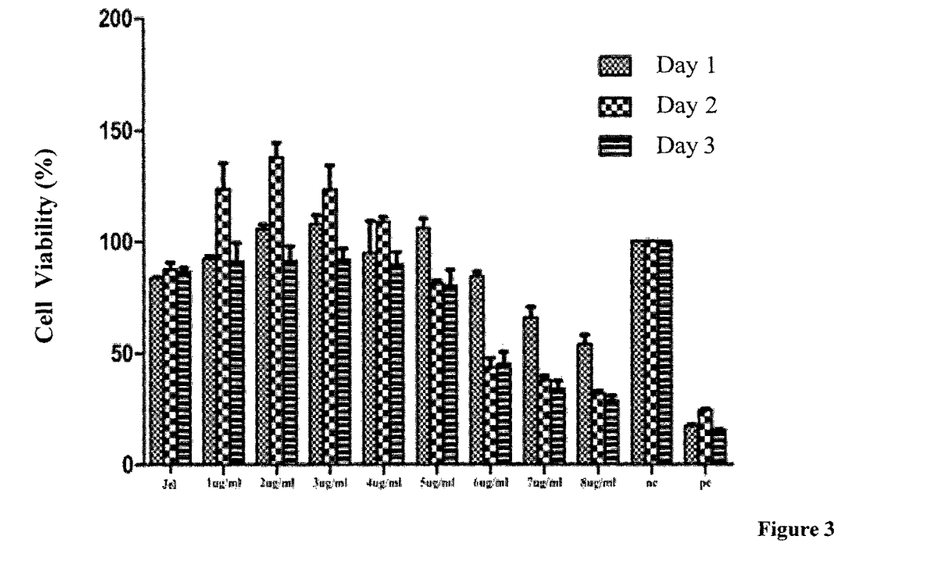
FIG. 3 shows the effect of the gel combination and sodium pentaborate pentahydrate, which is used as the active ingredient, at eight different high concentrations in the range of 1-8 mg/ml on L929 cell viability.

With the purpose of finding out whether sodium pentaborate pentahydrate used as an active ingredient within the gel combination has negative effects on cell viability at high concentrations in in vitro conditions, toxicity analyses were conducted for three days for the gel mixture prepared within carbopol used as 8 different concentrations ranging between 1 and 8 mg/ml and a carrier molecule. When analyzed statistically, a significant amount of toxic effect was determined at concentrations higher than 5 mg/ml (FIG. 3).

Figure 4:
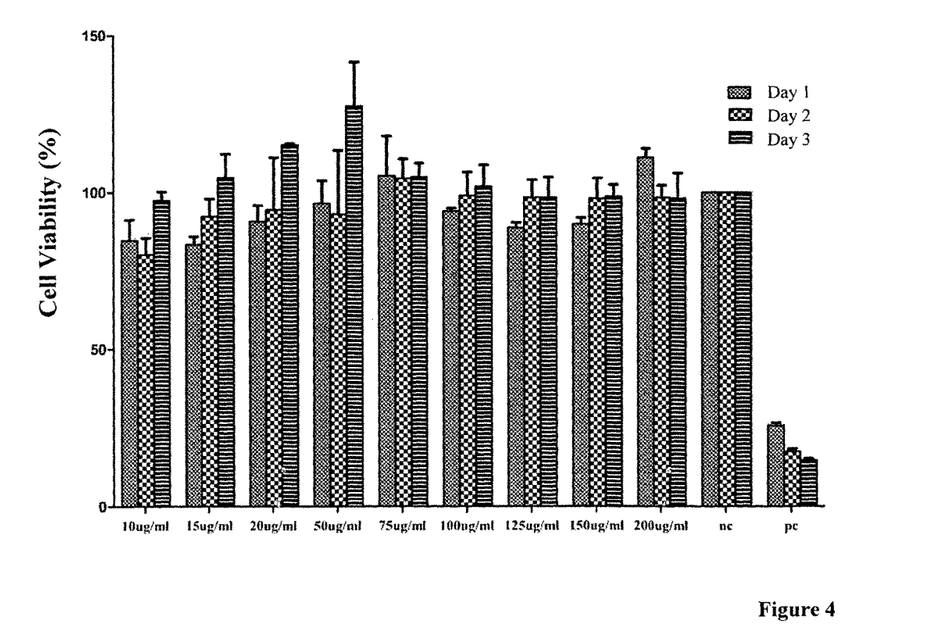
FIG. 4 shows the effect of sodium pentaborate pentahydrate, which is used as the active ingredient in the gel combination, at nine different high concentrations in the range of 10-200 µg/ml on human fibroblast cell viability.

Following the toxicity analyses conducted on mouse fibroblast cells, cell viability analyses on human fibroblast cell line were completed as well. Cell viability analyses were conducted on human fibroblast in in vitro conditions by using nine different concentrations ranging between 10 and 200 μg/ml. No toxic effect was observed at the applied concentrations (FIG. 4).

Figure 5:
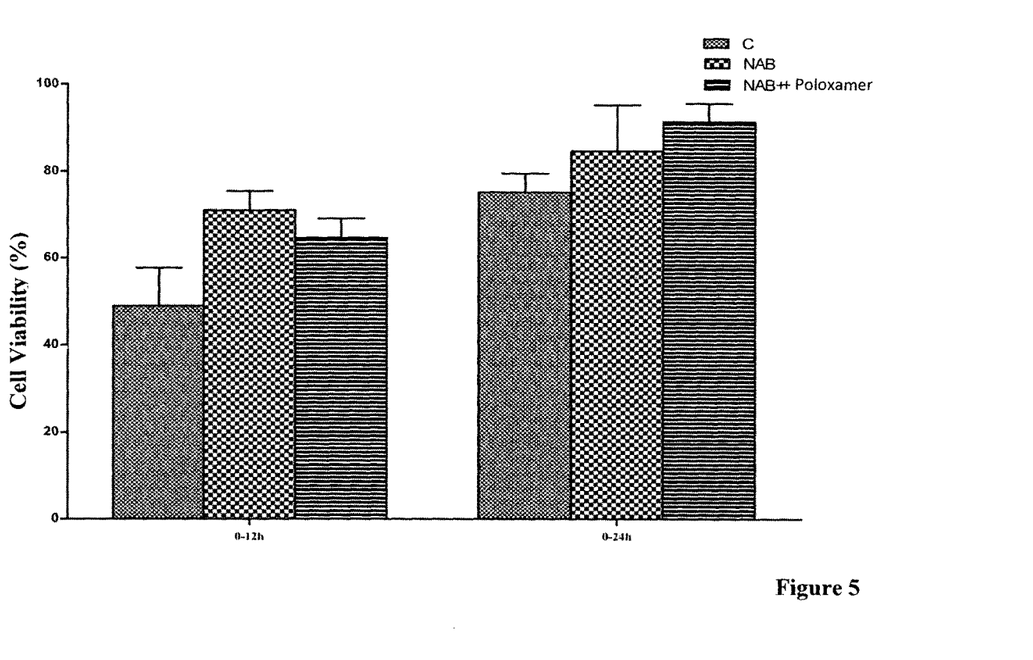
FIG. 5 is the view of the effect of the gel combination and different combinations of the molecules used in the combination on L929 in vitro wound closure.

In in vitro conditions, wound healing assay was performed by scratching the cells which are growing as a single layer and analyzing healing by photographing the wound area at certain time periods. A wound closure experiment was conducted with L929 cells in in vitro conditions in order to determine the activity of the prepared gel formulation on wound healing. The wound area was analyzed by NIH image program by photographing the wound are at 0, 12 and 24 hours. While in the first 12 hour period, sodium pentaborate pentahydrate used as active ingredient in the gel was more effective than the gel combination; at the end of 24 hour monitoring, it was determined that the gel combination substantially increased wound closure. At the end of 12 hours, approximately 49% closure was observed at the control group, while 71% and 64% closures were observed at the group to which sodium pentaborate pentahydrate and the gel combination were administered, respectively. At the end of 24 hours, while the wound closure rate of the control group was 75%, in the groups to which sodium pentaborate pentahydrate and gel combination were administered the wound closure rates were measured as 84% and 91%, respectively (FIG. 5).

Figure 6:
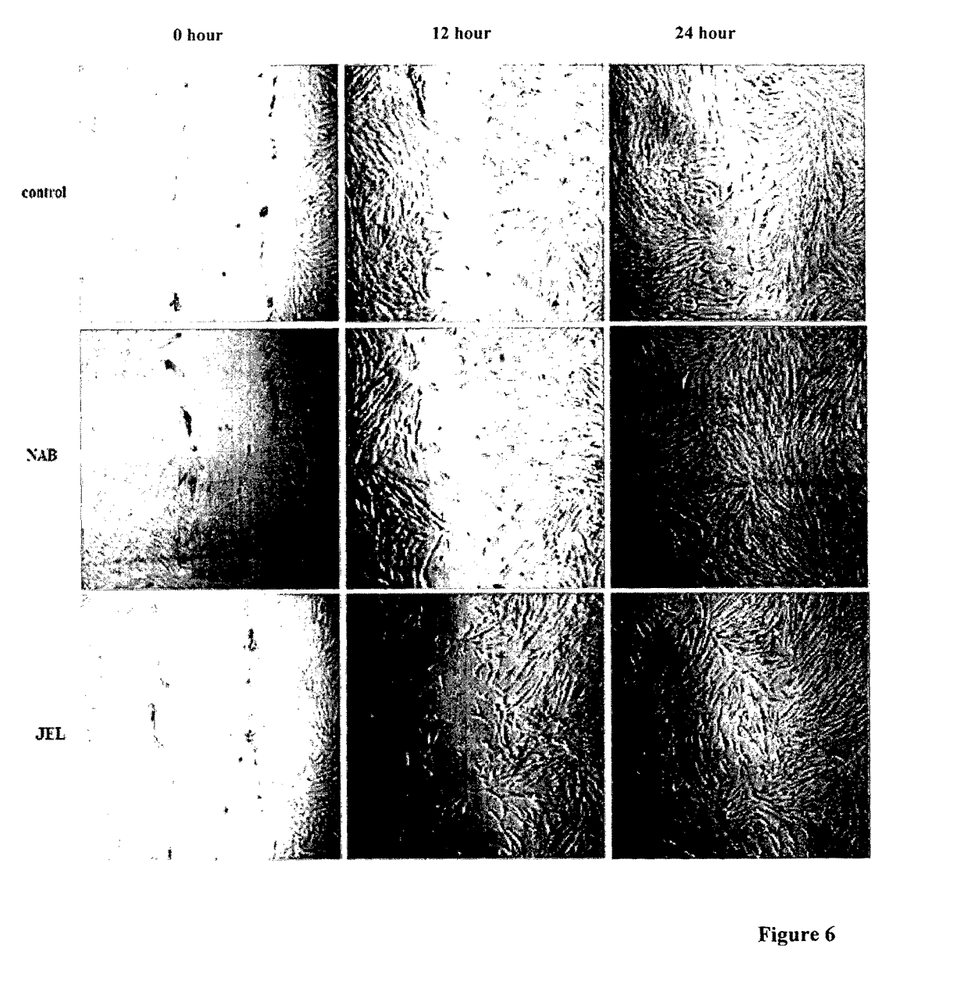
FIG. 6 is the view of in vitro wound closure on human fibroblast cells.

In vitro wound healing experiments were repeated by using human fibroblast cells. Wound closure was analyzed by taking photographs at 12 and 24 hours. When the wound closure rates were analyzed, it was determined that sodium pentaborate pentahydrate used in the gel was more effective on wound healing than the control group and get combination. At the end of a 12 hour period of time, the wound closure rate of the control group was determined as 39%, while the wound closure rates of the groups to which sodium pentaborate pentahydrate and gel combination were administered were 58% and 54%, respectively. At the end of 24 hours, the wound closure rate of the control group was measured as 67%, while the wound closure rates of the groups to which sodium pentaborate pentahydrate and gel combination were administered were measured as 91% and 85%, respectively (FIG. 6).

Figure 7:
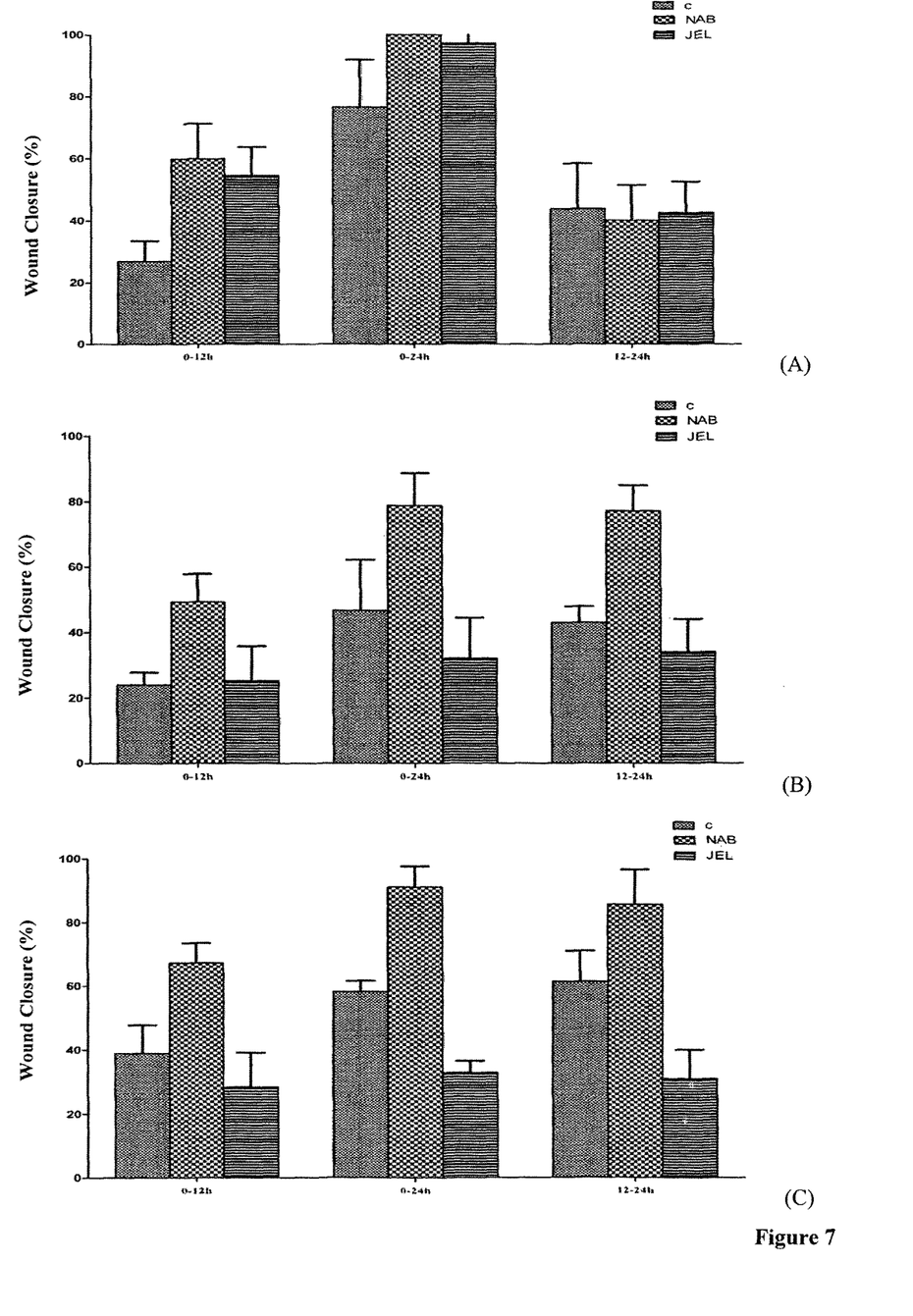
FIG. 7 is the view of results of in vitro wound closure of (a) L929/HUVEC co culture, (b) keratinocyte, and (c) human fibroblast wound closure.

Co-culture experiments were conducted to mimic the wound healing in the skin. Wound healing was analyzed by culturing L929 mouse fibroblast ceils and HUVEC endothelial cells in in vitro conditions. At the end of a 12 hour period of time, the wound closure rate of the control group was determined as 41%, while the wound closure rates of the groups to which sodium pentaborate pentahydrate and gel combination were administered were determined as 59% and 54%, respectively. At the end of 24 hours, the wound closure rate of the control group was measured as 76%, while the wound closure rates of the groups to which sodium pentaborate pentahydrate and gel combination were administered were measured as 100% and 97%, respectively. It was determined that the active ingredient sodium pentaborate pentahydrate and the gel combination were more effective on wound healing in comparison to the control group (FIG. 7).

Figure 8:
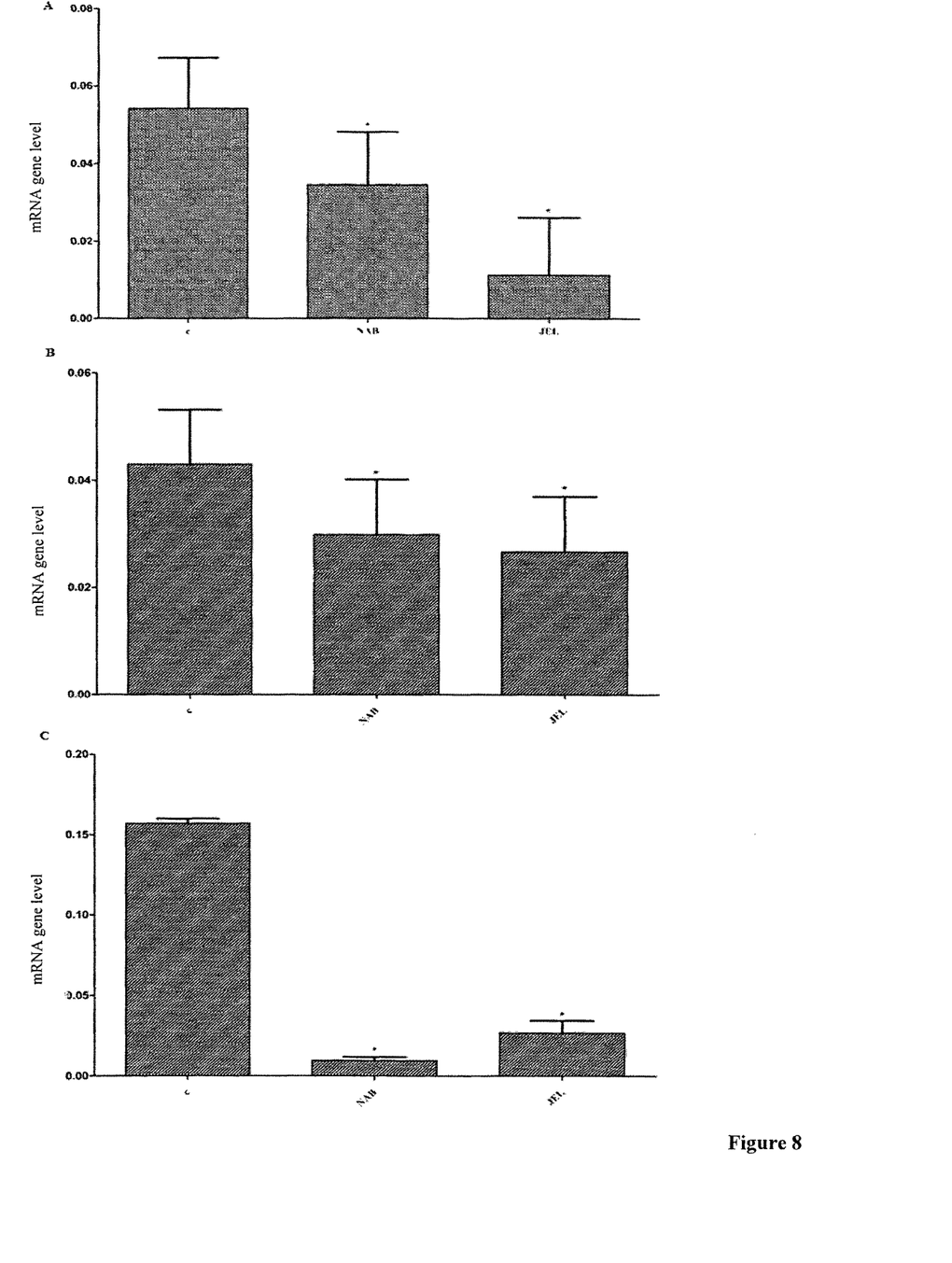
FIG. 8 is the view of the results of (a) Akt, (b) Bax and (c) p53 gene levels.

Real time PCR analyses were conducted in order to show the activity of the prepared gel combination on wound healing in gene expression level. The analyses conducted at gene expression level were completed by analyzing the genes affecting cell migration and the apoptotic genes. The decrease in the Akt gene levels is a factor that affects the wound closure in the cells and the decrease in the gene level is an indicator of the increase in cell migration (Jones et al., 2010). Bax and p53 genes play roles in apoptotic mechanism and the decrease in their expression levels is considered as an indicator of cell proliferation. The results of the analysis that was conducted showed that the gel combination and the active molecule used in the combination decreased apoptotie gene levels and akt gene levels (FIG. 8).

Oxidative stress is a factor which is effective in wound healing process and skin aging. With the activity of various antioxidant enzymes, the reactive oxygen species produced in the body and their harmful effects are eliminated. The effect of the gel combination developed in the present invention on antioxidant enzyme activity was determined by measuring the glutathione peroxidase, superoxide dismutase (SOD) and malondialdehyde (MDA) levels. Glutathione peroxidase, superoxide dismutase and malondialdehyde are used in the literature in wound healing studies as an indicator for observing the effects of oxidative stress. SOD converts superoxide ion to hydrogen peroxide and the resulting hydrogen peroxide is converted to water with glutathione peroxidase in lysozyme. Furthermore, MDA is also produced as a result of lipid peroxidation and causes mutations upon interacting with DNA. The increase in glutathione peroxidase and superoxide dismutase enzyme activity and the decrease in MDA level are considered as indicators of an effective wound healing (Bayati and Abdulla, 2012). The fact that glutathione peroxidase has protective effect in the inflammation step of wound healing is proved in the studies conducted (Munz et al., 1997). The glutathione peroxidase activity is indirectly measured by analyzing NADPH (Nicotinamide Adenine Dinucleotide Phosphate) oxidation based on absorbance. A substantial amount of enzyme activity was determined in the gel combination and sodium pentaborate pentahydrate groups in comparison to the control group. Superoxide dismutase enzyme activity was determined indirectly. The high level of enzyme activity was observed in the gel combination and sodium pentaborate pentahydrate groups.

When malondialdehyde levels, which are indicators of lipid peroxidation, were analyzed, low MDA levels were observed in the gel combination and sodium pentaborate pentahydrate groups in comparison to the control group. When oxidative stress parameters were examined, it was determined that sodium pentaborate pentahydrate group alone was more effective then the gel combination (FIG. 9).

Karyotype analyses were conducted in order to determine whether the prepared gel combination caused a chromosomal anomaly on the cells. The results showed that when sodium pentaborate pentahydrate and gel combination were applied, the cells maintained their normal karyotypes (FIG. 10).

By using the "Polymer based hydrogel" of the present invention; lotion, cream, emulsion, spray, foam, gelatin, paste, powder or plasters, skin plate and wound dressing textile products can be developed in different therapeutic compositions which are antimicrobial (antibacterial, anti-candidal, antifungal) and fast wound healing, and which prevent formations of wrinkles and scars.

All kinds of perfumes, moisturizers and surfactants, which will not chemically interact with the products in the formulations, can be added to the said hydrogel at suitable concentrations such that they will not reduce the antimicrobial, wound healing and anti-aging properties thereof.

The hydrogel formulation disclosed in the present patent document can be used in all medical products, personal care products, cosmetic applications, drug formulations and medical applications upon being optimized.

The invention claimed is:

1. An anti-aging, wound-healing and antimicrobial hydrogel, which is comprising: 3% boron compound, 4% poloxamer and 1% gel; wherein the boron compound and the poloxamer are added to the gel that is prepared as a carrier, wherein the boron compound is selected from a group consisting of sodium pentaborate pentahydrate, boric acid, alkaline and alkaline earth metal borates and all hydrate forms of these borates, ammonium borates, and boric acid esters.

2. The hydrogel according to claim 1, wherein the gel comprises carbopol.

3. The hydrogel according to claim 1, wherein the boron derivative is a sodium pentaborate pentahydrate.

4. The hydrogel according to claim 1, wherein a mixture of the gel, the boron compound and the poloxamer are stored at 4° C. for 16-24 hours before it can be used.

5. The hydrogel according to claim 1, wherein the boron compound is a boric acid.

6. The hydrogel according to claim 1, wherein the boron compound is alkaline metal borates.

7. The hydrogel according to claim 1, wherein the boron compound is alkaline earth metal borates.

8. The hydrogel according to claim 1, wherein the form of the hydrogel is selected from a group consisting of lotion, cream, emulsion, spray, foam, gelatin, paste, powder, plaster, skin plate, and wound dressing textile product.

* * * * *